United States Patent [19]
Bohls

[11] Patent Number: 5,935,095
[45] Date of Patent: Aug. 10, 1999

[54] EXTERNAL SLOT VALVE FOR CONTROLLING BLOOD FLOW THROUGH THE OUTLET OF A SHUNT OF A CARDIOPULMONARY BYPASS PUMP

[76] Inventor: Fred O. Bohls, 2103 Meadowbrook, Austin, Tex. 78703

[21] Appl. No.: 08/911,029

[22] Filed: Aug. 14, 1997

[51] Int. Cl.⁶ .................................................... A61M 5/00
[52] U.S. Cl. ................................................. 604/9; 600/16
[58] Field of Search ...................... 604/4–10; 600/16–18; 623/3

[56] References Cited

U.S. PATENT DOCUMENTS 4,553,532  11/1985  Bohls .
5,383,839   1/1995  Bohls .

Primary Examiner—John G. Weiss
Assistant Examiner—Ki Yong O
Attorney, Agent, or Firm—Brady, O'Boyle & Gates

[57] ABSTRACT

An external slot valve for controlling blood flow through the outlet of a shunt of a cardiopulmonary bypass pump wherein a valve seat having a knife edge is fixedly connected to the fixed plate of the bypass pump, and a valve head having a knife edge is pivotally connected to the fixed plate. The valve head is spring biased to the closed position against the valve seat to pinch the shunt extending therethrough. When in the open position, the knife edges provide a slot forming a large orifice for the blood to flow through the outlet of the shunt to diminish the work of the pump and reduce trauma to the blood.

5 Claims, 3 Drawing Sheets

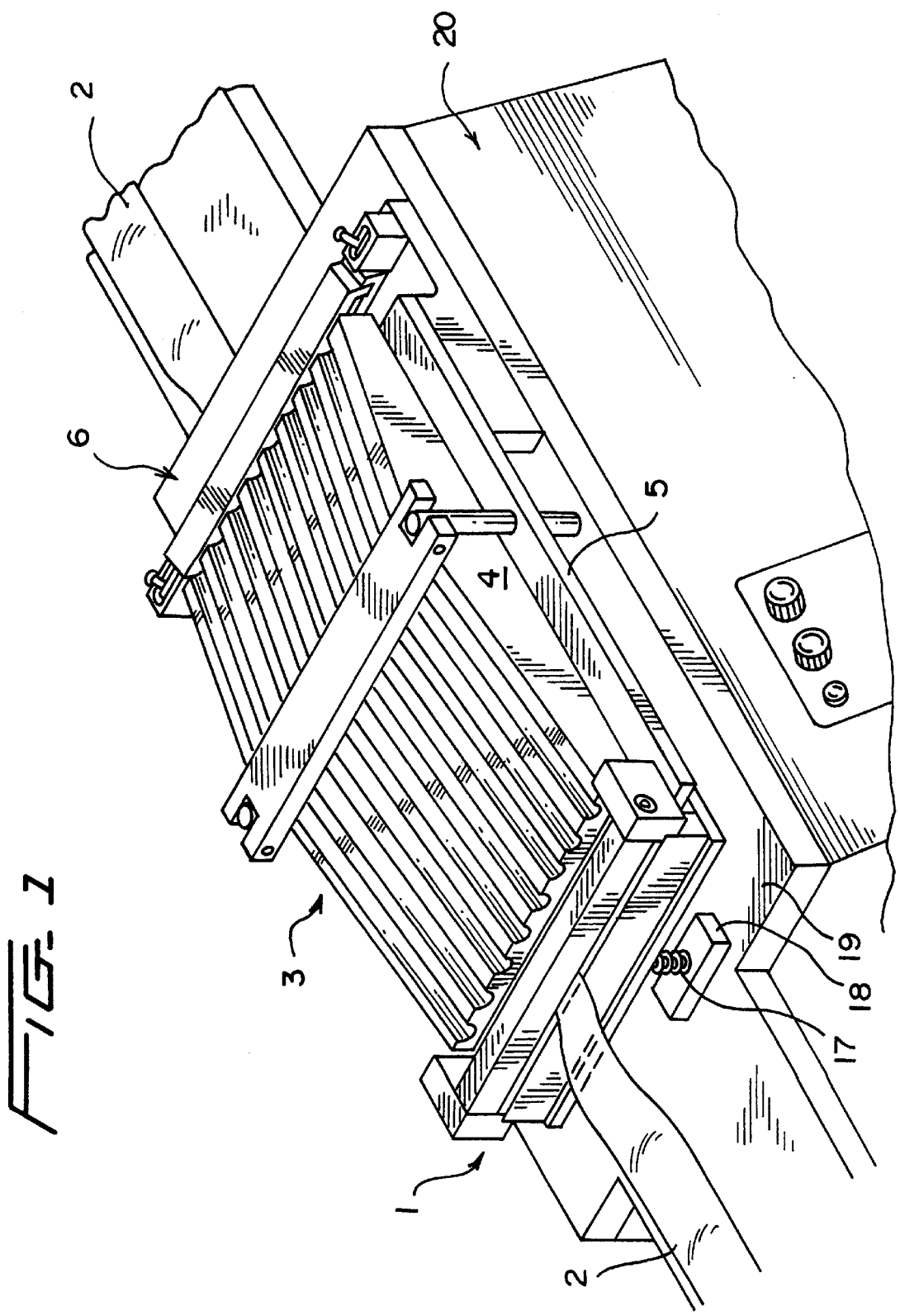

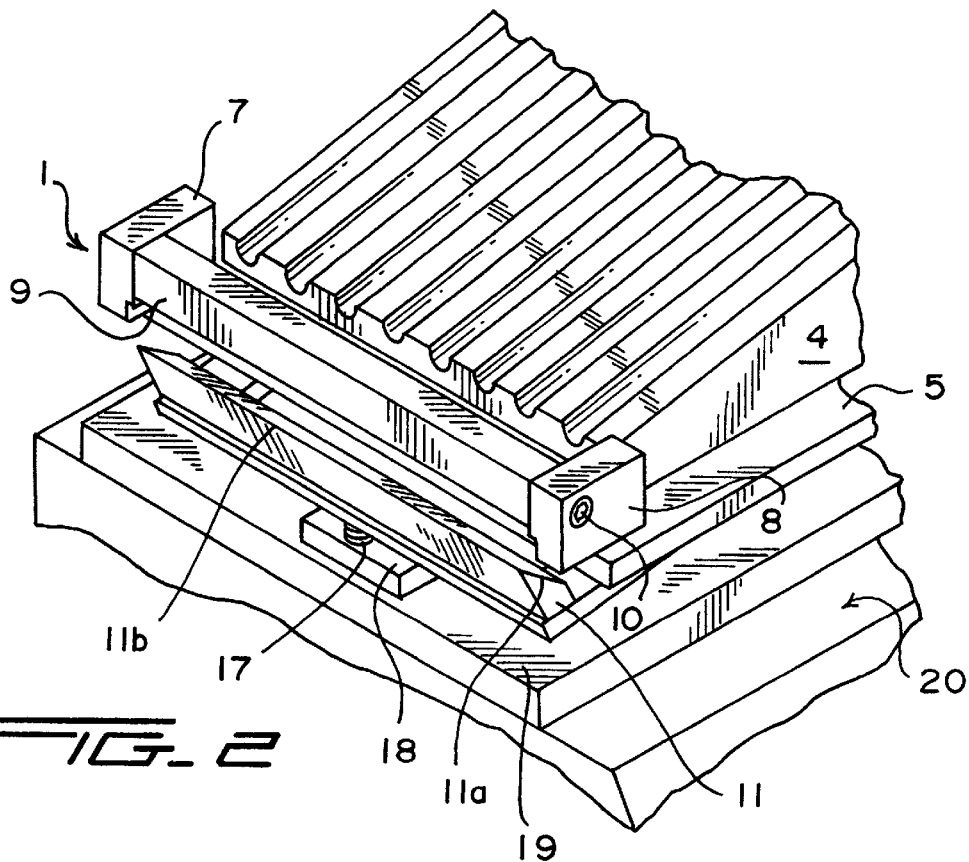
FIG_2
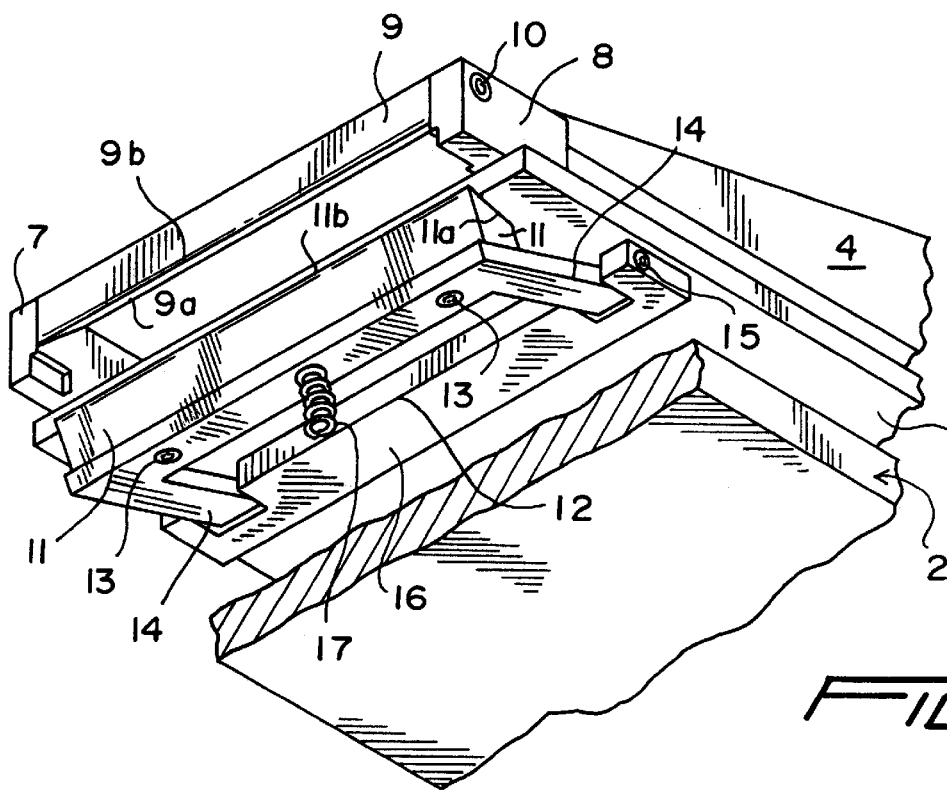
FIG_3

EXTERNAL SLOT VALVE FOR CONTROLLING BLOOD FLOW THROUGH THE OUTLET OF A SHUNT OF A CARDIOPULMONARY BYPASS PUMP

BACKGROUND OF THE INVENTION

Externally valved shunts for a cardiopulmonary bypass pump are disclosed in U.S. Pat. No. 4,553,532 dated Nov. 19, 1985 and U.S. Pat. No. 5,383,839 dated Jan. 24, 1995, wherein roller-like valve elements and external plate valves are positioned at the inlet and outlet of a compressible tubing shunt for controlling the flow of blood through the tubing mounted in the compression chamber of a pulsatile flow pump.

While the roller-like valve elements and external plate valves have performed their intended function, the slot valve of the present invention is an improvement thereon in that the slot valve of the present invention provides a larger orifice for the blood to flow through, thereby diminishing the work of the pump, and reducing the velocity of the blood flow through the outlet slot valve, thus, lessening the shear stress upon the red blood cells and other particulate matter, such as the large molecules, albumin, and globulin, whereby trauma to the blood is reduced.

SUMMARY OF THE INVENTION

The external slot valve of the present invention comprises, essentially, a first component fixedly mounted on the end of the fixed plate of the cardiopulmonary bypass pump and including a depending bevelled knife edge portion. A second component is pivotally mounted to the end of the fixed plate of the bypass pump and includes an upwardly extending bevelled knife edge portion aligned with, and spaced below, the knife edge portion on the first component. The space between the knife edge portions provides a slot through which the shunt carrying the blood extends, and a spring is interposed the second component and a back plate positioned below the fixed plate of the bypass pump for biasing the upwardly extending knife edge portion in a direction toward the shunt.

By this construction and arrangement, during the down stroke of the movable compression plate of the pump, the upwardly extending knife edge on the slot valve at the outlet of the pump is pivoted downwardly against the biasing force of the spring to open the slot allowing the blood to flow from the shunt.

BRIEF DESCRIPTION OF THE DRAWINGS

FIG. 1 is a perspective view of a cardiopulmonary bypass pump showing the slot valve of the present invention positioned at the outlet of the pump;

FIG. 2 is a fragmentary perspective view of the slot valve in the open portion;

FIG. 3 is a fragmentary perspective view of the slot valve shown in FIG. 2 as viewed from the bottom;

DESCRIPTION OF THE PREFERRED EMBODIMENTS

Figure 4:
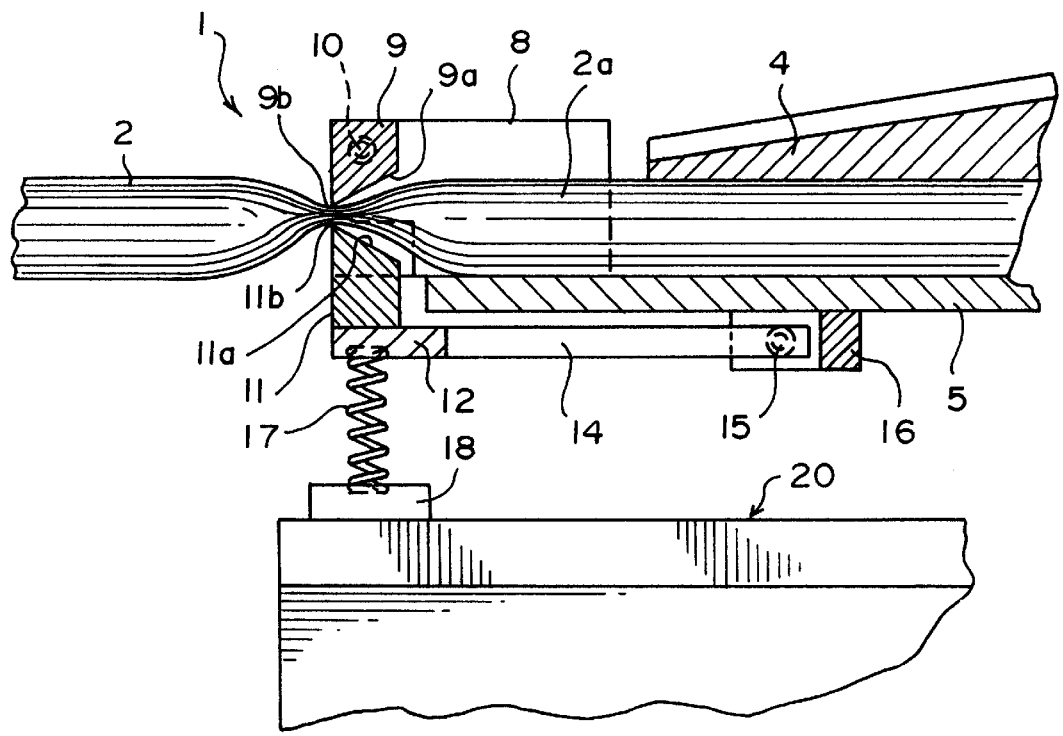
FIG. 4 is a fragmentary, sectional side elevational view showing the slot valve in the closed position.

Referring to the drawings and, more particularly to FIG. 1, the external slot valve 1 of the present invention is constructed and arranged for controlling the blood flow through the outlet of a compressible shunt 2 of a cardiopulmonary bypass pump 3 of the type disclosed in U.S. Pat. No. 4,553,532 dated Nov. 19, 1985 and U.S. Pat. No. 5,383,839 dated Jan. 24, 1995 which include a movable compression plate 4 and a fixed compression plate 5. The external inlet valve 6 is a pinch valve of the type disclosed in U.S. Pat. No. 5,383,839, the description of which is incorporated herein by reference.

The details of the construction of the external slot valve 1 are illustrated in FIGS. 2 and 3, wherein a first component is provided comprising a pair of transversely spaced blocks 7 and 8 integrally connected to the upper surface of the fixed compression plate 5 of the pump at the outlet end thereof. A transversely extending bar 9 is positioned between the blocks 7 and 8 and fixedly connected at each end thereof to the blocks 7 and 8 by suitable bolts 10. The bottom wall of the bar 9 is provided with a downwardly bevelled surface 9a terminating in a knife edge 9b.

A second component of the slot valve 1 is connected to the bottom surface of the fixed compression plate 5 and comprises a transversely extending bar 11 having an upwardly bevelled surface 11a terminating in a knife edge 11b. The bar 11 is supported on a transversely extending plate 12 and fixedly connected thereto by bolts 13. Each end of the transversely extending plate 12 is provided with an arm 14 having one end integral with the plate 12 and the opposite end being pivotally connected as at 15 to a bracket 16 fixedly connected to the bottom surface of the fixed plate 5 of the pump.

A spring 17 is positioned between the lower surface of the plate 12 and the upper surface of a base plate 18 supported on the top wall 19 of the pump housing 20. By this construction and arrangement, the lower bar 11 and associated knife edge 11b provides a valve head biased upwardly in a direction toward the upper bar 9 and associated knife edge 9b which provide a valve seat, whereby the slot valve 1 is biased to the closed position.

Referring to FIGS. 1 and 3, the portion of the shunt 2 extending between the inlet valve 6 and outlet valve 1 forms a sack 2a.

In the operation of the inlet valve 6 and outlet valve 1 for controlling blood flow through the shunt 2 of the cardiopulmonary bypass pump 3, the inlet valve 6 is initially open to allow blood to flow into the sack 2a. The outlet valve 1 is in the closed position wherein the spring 12 biases the bar 11 and associated knife edge 11b upwardly toward the knife edge 9b on bar 9 to thereby pinch the shunt 2.

Figure 5:
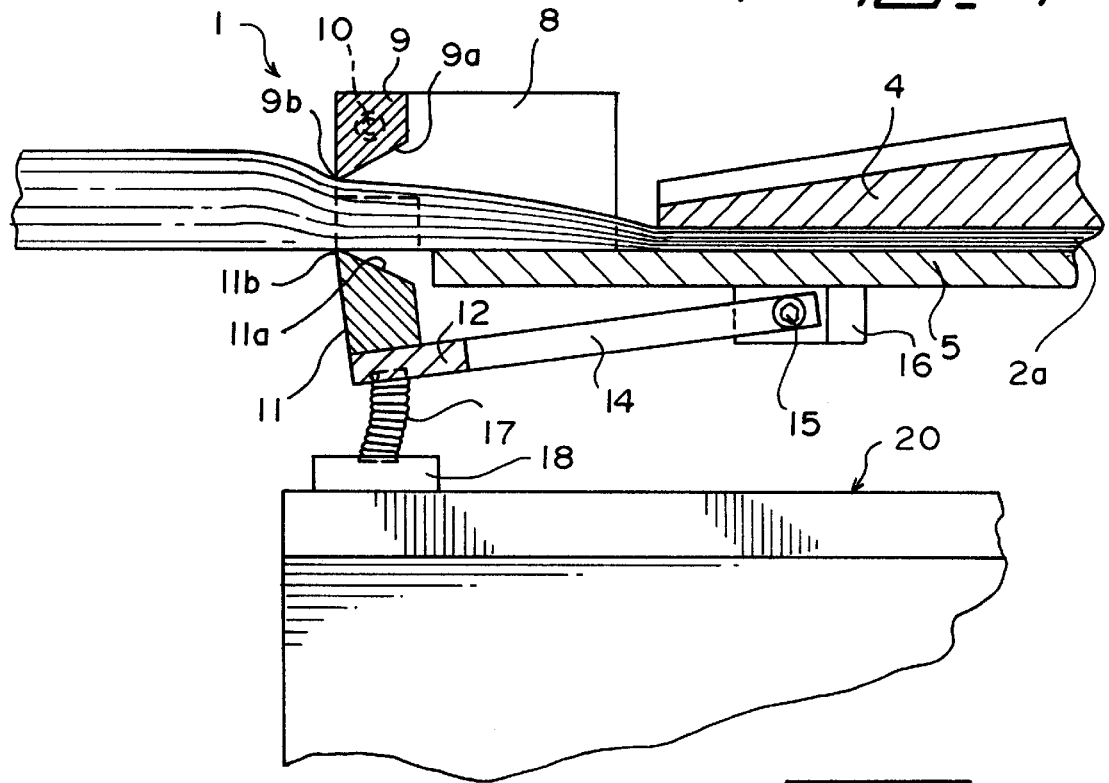
FIG. 5 is a fragmentary, sectional side elevational view showing the slot valve in the open position.

The opening of the inlet valve 6 and closing of the outlet valve 1 occurs because the systemic pressure in the shunt 2 is greater than the pressure in the sack 2a. When the compression plate 4 compresses the sack 2a, as shown in FIG. 5, the pressure in the sack 2a is greater than the upstream pressure in the shunt 2 causing the inlet valve 6 to pinch the shunt to the closed position, as described in the aforementioned U.S. Pat. No. 5,383,839. Since the pressure in the sack 2a is greater than the downstream systemic pressure in the shunt 2, the bar 11 and associated knife edge 11b are caused to pivot downwardly away from the knife edge 9b to the open position, thereby providing a slot to permit an outflow of blood from the compressed sack 2a.

When the compression plate 4 returns to the position shown in FIG. 4, the sack 2a fills passively since the upstream reserve pressure is greater than the pressure in the sack 2a, whereby the inlet valve 6 is moved to the open position, and the outlet valve 1 is moved to the closed position because systemic pressure is once again greater than the pressure within the sack 2a.

From the above description, it will be readily appreciated by those skilled in the art that the external slot valve of the present invention for controlling blood flow through the outlet of a shunt of a cardiopulmonary bypass pump is an improvement over other outlet valves in that the slot valve of the present invention provides a larger orifice for the blood to flow through, thereby diminishing the work of the pump 3, and reducing the velocity of the blood flow through the outlet slot valve 1, thus lessening the shear stress upon the red blood cells and other particulate matter, such as the large molecules, albumin, and globulin, whereby trauma to the blood is reduced.

It is to be understood that the form of the invention herewith shown and described is to be taken as a preferred example of the same, and that various changes in the shape, size, and arrangement of parts may be resorted to, without departing from, the spirit of the invention or scope of the subjoined claims.

I claim:

1. An external slot valve for controlling blood flow through the outlet of a shunt of a cardiopulmonary bypass pump having a movable compression plate, a fixed plate, and external inlet pinch valve and a compressible shunt for conveying blood through a patient, said shunt extending through said external inlet pinch valve and said external slot valve, said slot valve comprising means for providing a valve seat fixedly mounted on the fixed plate of the bypass pump, and means for providing a movable valve head connected to the fixed plate of the bypass pump, and means for biasing the valve head to the closed position against the valve seat, to thereby pinch the shunt to the closed position.

2. An external slot valve according to claim 1, wherein the means for providing the valve seat comprises a pair of transversely spaced blocks fixedly connected to an upper surface of the fixed plate of the bypass pump, a first transversely extending bar positioned between said blocks, means for fastening each end of said bar to said blocks, a depending knife edge provided on said first bar, said valve head comprising a transversely extending plate positioned below the fixed plate of said bypass pump, a second transversely extending bar mounted on said plate, and an upwardly extending knife edge provided on said second bar.

3. An external slot valve according to claim 2, wherein at least one arm extends between the transversely extending plate and a lower surface of the fixed plate of the bypass pump, said arm having one end fixedly connected to said transversely extending plate, and means for pivoting another end of said arm to the lower surface of the fixed plate of the bypass pump.

4. An external slot valve according to claim 3, wherein the means for biasing the valve head to the closed position comprises a fixed base plate, and a spring mounted between said fixed base plate and said transversely extending plate.

5. An external slot valve according to claim 2 wherein said first and second bars, each have bevelled surfaces terminating in the respective knife edges.

* * * * *